Jan. 8, 1974 B. J. MACHIN Plant Pat. 3,425
CHRYSANTHEMUM PLANT
Filed Dec. 27, 1971
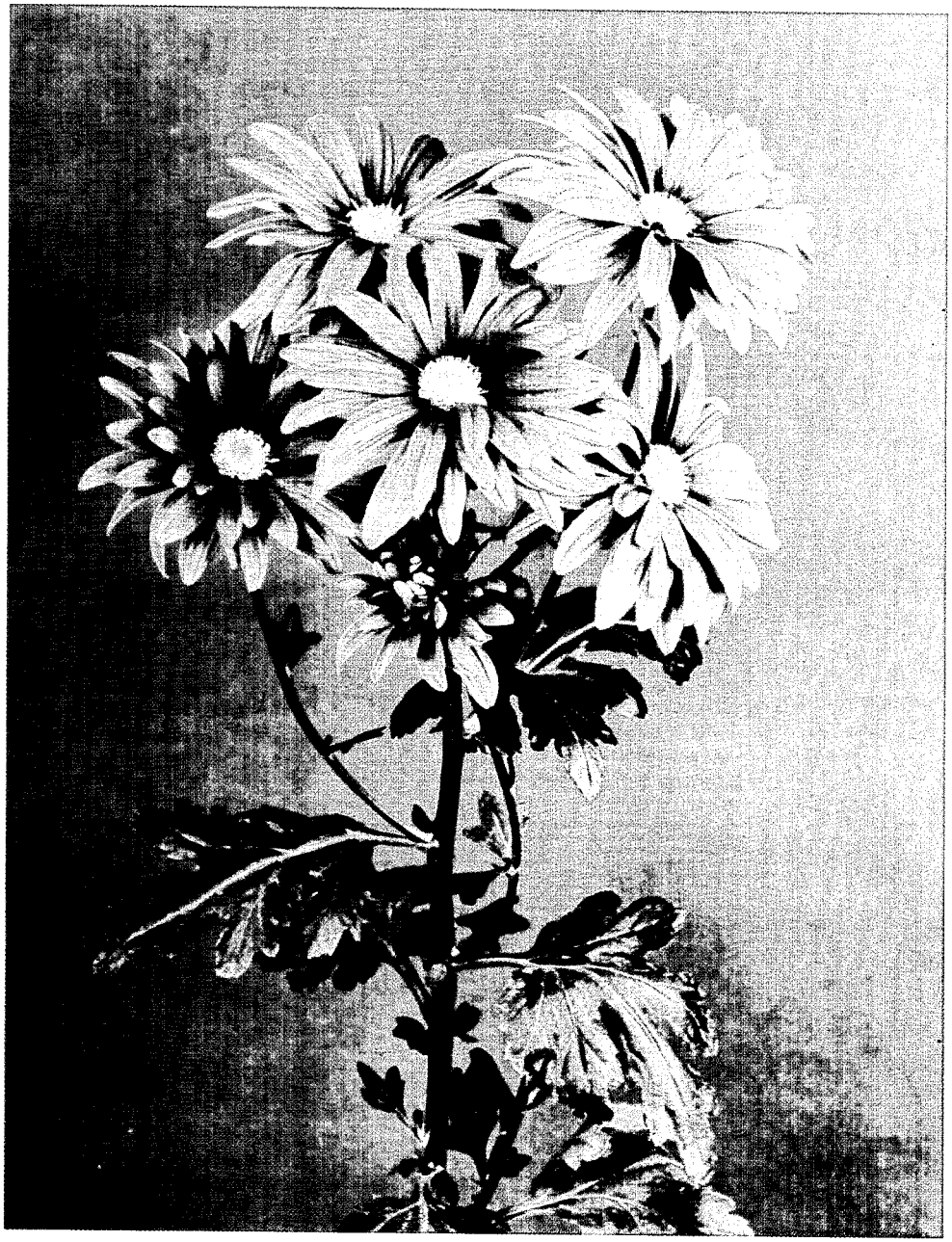

United States Patent Office

Plant Pat. 3,425
Patented Jan. 8, 1974

3,425
CHRYSANTHEMUM PLANT

Barrie John Machin, East Broyle Estate, Chichester, England, assignor to Frampton's Nurseries Limited, Chichester, Sussex, England Filed Dec. 27, 1971, Ser. No. 212,834
Int. Cl. A01h 5/00
U.S. Cl. Plt.—74 1 Claim This invention relates to a new and distinct variety of *Chrysanthemum morifolium* Bailey (spray type) known as Nero. Nero is a seedling originated by me from a cross made in 1967 between the unpatented variety Tuneful and the unpatented variety Delight, the formed being the seed parent, and the latter being the pollen parent.

The variety Nero resulted from an extensive breeding program with the object of producing improved varieties for year round chrysanthemum production programs with more vigor and reduced flowering time compared with existing varieties. The immediate objective was to improve the varieties Tuneful and Delight which, in Southern England, required a total of 13 or 14 weeks for single stem flowering during the summer.

Nero is characterized by the following unique combination of improved characteristics:

(1) It is extremely vigorous and will produce flowering crops in 12 weeks from rooted cuttings during the summer and 16 weeks from rooted cuttings during the winter.
(2) Despite its extreme vigor it is also responsive and will set buds and flower uniformly in a wide range of environmental conditions.
(3) Its color is bright red bronze comparing very favorably with other red bronze singles and holding well in high temperature conditions.

As compared with its seed parent, Nero has more vigor, can be flowered in less total growing time round the year, and will not fail to flower or flower late under high temperature conditions. During poor light conditions the seed parent Tuneful may become devernalized and develop a rosetted habit of growth, but Nero does not suffer from this fault. Tuneful is a variety which attracts aphids and bad infestations can occur where this variety is grown. Nero is much less attractive to aphids.

As compared with its pollen parent, Nero is more vigorous, producing a longer flowering stem under a similar number of longday conditions. In winter conditions the foliage of the pollen parent, Delight, can be pale green and rather gross. Nero, on the other hand, has dark green luxuriant foliage which is never extremely vegetative.

The variety which Nero rembles most in color is Red Delight, a natural sport from Delight. Nero is lighter in color than Red Delight and has more bronze undertones in it. Moreover the flowers of Nero are larger and are displayed to better advantage on the spray.

Asexual reproduction of this new variety Nero by rooting vegetative shoots in Sussex, England, shows that the above characteristics are fixed and come true to type in succeeding generations.

The accompanying drawing shows a typical flower of my new variety depicted in color as nearly true as it is reasonably possible to make the same in a color illustration of this character.

The following is a detailed description of the new variety Nero with color terminology in accordance with the Royal Horticultural Society Color Chart, hereinafter referred to as RHS.

Genus: Chrysanthemum.
Species: Morifolium Bailey.
Type: Spray.
Class: Single.
Breeding: Original seedling resulting from a cross between the variety Tuneful, the seed parent, and Delight, the pollen parent. The cross was made in 1967 at Frampton's Nurseries Ltd., Forbridge Nursery, Chichester, Sussex, England.
Propagation: Holds its distinguishing characteristics through succeeding propagations by rooting vegetative shoots.
Flower: When grown and observed in Sussex, England, 6 to 12 flowers are born on pedicels after removal of the main apical bud.
Bloom:
*Size.*—Average diameter is 10 cm. when fully open.
*Petalage.*—Single—approximately 50 ray petals. Diameter of disc is 1¾ to 2 cm.
Bloom:
*Form.*—Single, with flat, slightly reflexing petals.
*Petals.*—Long, broad, overlapping, blunt, and with medium texture.
*Pedicels.*—Thick and 10 to 12 cm. in length.
Color of open bloom:
Inner face of fully expanded ray petal RHS 42B.
Outer face of fully expanded ray petal RHS 20C.
Inner face of young ray petal RHS 46A.
Outer face of young ray petal RHS 20B.
Inner and outer faces of disc petals RHS 7A.
Response Group: 10 weeks.
Temperature tolerance: 55–60° F. at night.
Plant: Strong upright habit of growth.
Foliage:
Medium quality average internode length 3 cm.
Medium to large size.
Color RHS 137B.
Texture medium.
Stem: Thick and strong. Color 143C at flowering—water uptake good.

I claim:

1. A new and distinct variety of *Chrysanthemum morifolium* Bailey, spray type, substantially as shown and described, characterized particularly as to novelty by the unique combination of a red bronze color, extreme vigor, and ability to set buds and flower uniformly in a wide range of environmental conditions.

No references cited.

ROBERT E. BAGWILL, Primary Examiner